(12) United States Patent
Rueb

(10) Patent No.: US 9,442,075 B2
(45) Date of Patent: Sep. 13, 2016

(54) GALVANOMETER SCANNED CAMERA WITH VARIABLE FOCUS AND METHOD

(71) Applicant: Virtek Vision International Inc., Waterloo (CA)

(72) Inventor: Kurt D. Rueb, Kitchner (CA)

(73) Assignee: VIRTEK VISION INTERNATIONAL INC., Waterloo, Ontario (CA)

( * ) Notice: Subject to any disclaimer, the term of this patent is extended or adjusted under 35 U.S.C. 154(b) by 413 days.

(21) Appl. No.: 14/200,204

(22) Filed: Mar. 7, 2014

(65) Prior Publication Data

US 2014/0253719 A1   Sep. 11, 2014

Related U.S. Application Data

(60) Provisional application No. 61/774,656, filed on Mar. 8, 2013.

(51) Int. Cl.
| | |
|---|---|
| *G01N 21/88* | (2006.01) |
| *H04N 5/232* | (2006.01) |
| *G02B 26/10* | (2006.01) |
| *G03B 17/17* | (2006.01) |
| *G02B 7/08* | (2006.01) |

(52) U.S. Cl.
CPC ............. *G01N 21/8806* (2013.01); *G02B 7/08* (2013.01); *G02B 26/105* (2013.01); *G03B 17/17* (2013.01); *H04N 5/23212* (2013.01); *H04N 5/23296* (2013.01); *G03B 2205/0046* (2013.01)

(58) Field of Classification Search
CPC ...................... G01N 21/8806; H04N 5/23212; H04N 5/23296; G02B 26/105
USPC ..................................................... 250/559.45
See application file for complete search history.

(56) References Cited

U.S. PATENT DOCUMENTS

| | | | |
|---|---|---|---|
| 5,615,013 A | 3/1997 | Rueb et al. | |
| 2001/0019444 A1* | 9/2001 | Takada | G02B 26/125 359/207.1 |
| 2011/0141463 A1* | 6/2011 | Chikamatsu | G01N 21/956 356/237.5 |
| 2012/0098947 A1* | 4/2012 | Wilkes | H04N 5/23212 348/65 |
| 2013/0342673 A1* | 12/2013 | Sticker | G02B 21/244 348/79 |

* cited by examiner

*Primary Examiner* — Seung C Sohn
(74) *Attorney, Agent, or Firm* — Warner Norcross & Judd LLP

(57) ABSTRACT

A camera assembly for generating a high resolution image of an area of interest on a workpiece includes a sensor array and an optical lens that focuses light reflected from the workpiece onto the sensor array. The sensor array is inclined relative to an optical axis defined by the optical lens disposed in a fixed position relative to the optical lens. A galvanometer driven mirror assembly directs a field of view of the optical lens toward the area of interest on the workpiece translating light reflected from the area of interest of the workpiece onto the sensor array. The inclination of the sensor array provides varying degrees of resolution relative to a distance of the workpiece area of interest from the camera assembly enabling the camera assembly to generate high resolution images at varying distances from the camera assembly without adjusting the optical lens relative to the sensor array.

22 Claims, 5 Drawing Sheets

GALVANOMETER SCANNED CAMERA WITH VARIABLE FOCUS AND METHOD

PRIOR APPLICATIONS

The present application claims priority to U.S. Provisional Application No. 61/774,656 filed Mar. 8, 2013.

TECHNICAL FIELD

The present application relates generally toward a method for inspecting a workpiece. More specifically, the present application relates to generating a high resolution image of an area of interest of a workpiece.

BACKGROUND

Vision systems used to inspect the quality of manufactured components are becoming more prevalent in industrial settings to ensure the quality of the manufactured product. For example, composite materials used in aerospace for reducing weight of an airplane require a high degree of integrity. There is an unrealized desire to inspect the fiber orientation and placement of carbon fiber material used in the construction of these aerospace components using a vision system from a distance. Additionally, weld quality, dimensional stability, and other areas of manufactured products that require a quality inspection are increasingly monitored by way of a vision system or assembly. A typical vision system consists of camera and lens assembly which can generally image a wide field of view at low resolution, for example using a wide angle lens, or a narrow field of view at high resolution, for example, using a telephoto lens precisely focused on a specific area of interest. However, applications such as imaging a large aerospace component at a level sufficient to resolve fibers used in the material, requires high resolution and a wide field of view to encompass the large scale of the component, which reduces resolution to level making a vision system of this type impractical. One attempt to address the limitations of these systems is by the vision system assembly using galvanometer scanning mirrors generally shown at 10 of FIG. 1. A camera 12 is orientated so that its field of view 14 is directed toward a first mirror 16, which directs the field of view 14 toward a second mirror 18, and subsequently onto a workpiece 20.

An angular orientation of the first mirror 16 relative to the field of view 14 of the camera 12 is controlled by a first galvanometer 22. In a like manner, an angular orientation of the second mirror 18 relative to the field of view 14 of the camera 12 is controlled by a second galvanometer 24.

This arrangement combined with appropriate selection of the camera resolution and lens field of view can provide arbitrary levels of theoretical resolution. For example, a telephoto lens can be selected such that the resolution of a single element of a high resolution camera sensor can correspond to a few thousandths of an inch resolution over entire parts spanning multiple feet. However, this sensor spatial resolution is ineffective if the image on the sensor is not precisely focused and is blurred across a large number of pixels on the sensor rendering this alternative impractical for the types of applications that would be most benefitted. A further problem with this arrangement is that focusing the camera 12 upon, in particular, a three-dimensional surface has proven slow, rendering this type of arrangement inefficient in a rapid manufacturing process. Although the galvanometers are known to move the field of view 14 of the camera 12 in a two-dimensional (X,Y) environment, the focus of the camera 12 is ineffective in a three-dimensional environment. This type of arrangement is generally disclosed in U.S. Pat. No. 5,615,013 to the same inventor of the present application, the content of which is incorporated herein by reference.

FIG. 2 shows an attempt to adjust the focus of the camera 12 in a three-dimensional direction making use of a similar galvanometer and mirror arrangement. In this arrangement, a CCD or CMOS the sensor array 26 is used to capture an image along the field of view 14 of the camera. A lens 28 is moved along an axis a of the field of view 14 of the camera 12 by way of a translation mechanism 30. However, the translation mechanism 30 used to move the lens 28 to enhance image clarity along a z axis of a three-dimensional surface is exceedingly costly and too slow to meet the demands of modern manufacturing systems. Additionally, the lens translation mechanism 30 is cumbersome and cannot be packaged into a small area. Furthermore, any deviations in the position of the lens from the axis of translation, even by a distance of microns, produces an offset in the imaged position generated by camera 12, making accurate measurements impossible. Therefore, it would be desirable to provide a more consistently accurate, rapid and cost-efficient method to generate a high resolution image along three axis of a workpiece.

SUMMARY

An inspection assembly for generating a high resolution image of a workpiece includes a sensor array and an optical lens defining an optical axis for focusing a view of the work piece onto the sensor array. A mirror assembly is oriented for redirecting the view of the sensor array. The sensor array is inclined relative to the optical axis of the optical lens. The orientation of the mirror assembly is adjusted for directing the view of the sensor array to an area of interest on the workpiece. The optical lens directs the view of the area of interest to a portion of the sensor array determined to produce a precisely focused image to increase the resolution of the image generated of the area of interest on the workpiece based upon the angle of inclination of the sensor array relative to the optical axis.

This arrangement provides a rapid focus of an area of interest of a workpiece with only adjusting the mirror assembly to direct the field of view of the camera to an area of interest on a workpiece. The optical lens of the inventive camera directs the field of view onto an area of the sensor array known to correlate with the most precisely focused, highest resolution image generated of the area of interest of the workpiece. Therefore, the position of the optical lens remains substantially constant relative to the sensor array requiring no moving parts to move the focal point of the camera along a depth of the workpiece to obtain a high resolution, precisely focused image. Because no moving components, other than the galvanometers, are included in the inventive assembly, a low cost, rapid, precisely focused inspection of a workpiece is achieved.

BRIEF DESCRIPTION OF THE DRAWINGS

Other advantages of the present invention will be readily appreciated, as the same becomes better understood by reference to the following detailed description when considered in connection with the accompanying drawings wherein.

DETAILED DESCRIPTION

Figure 1:
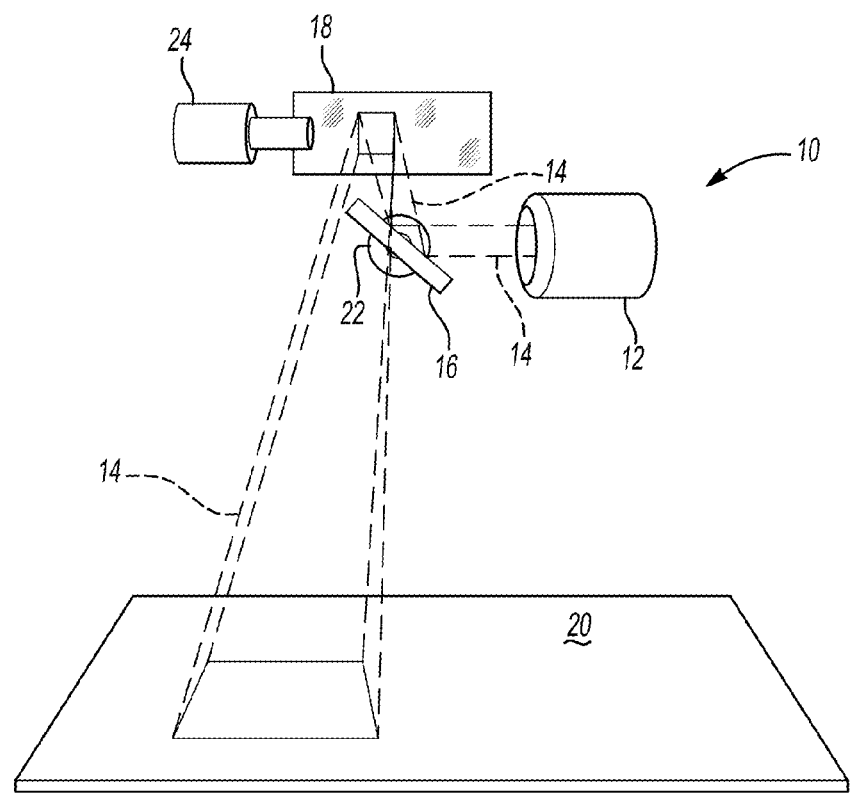
FIG. 1 shows a prior art embodiment of a vision system.
Figure 2:
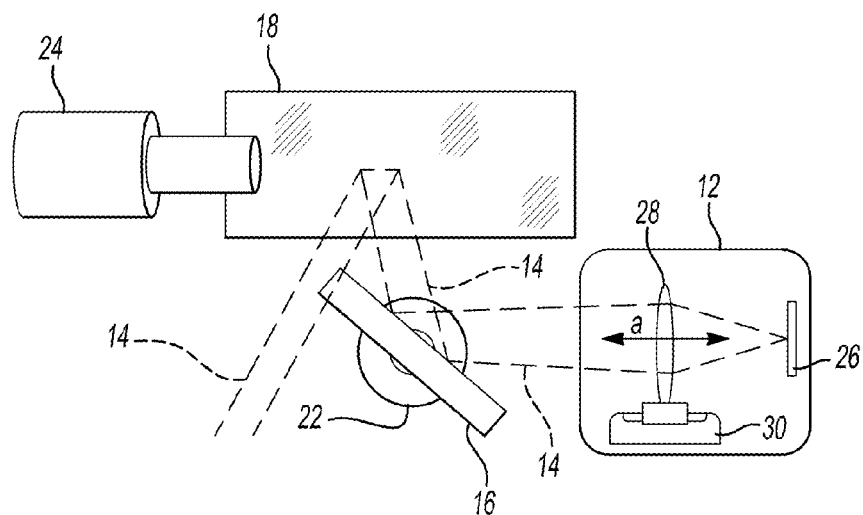
FIG. 2 shows a second prior art embodiment of a vision system.
Figure 3:
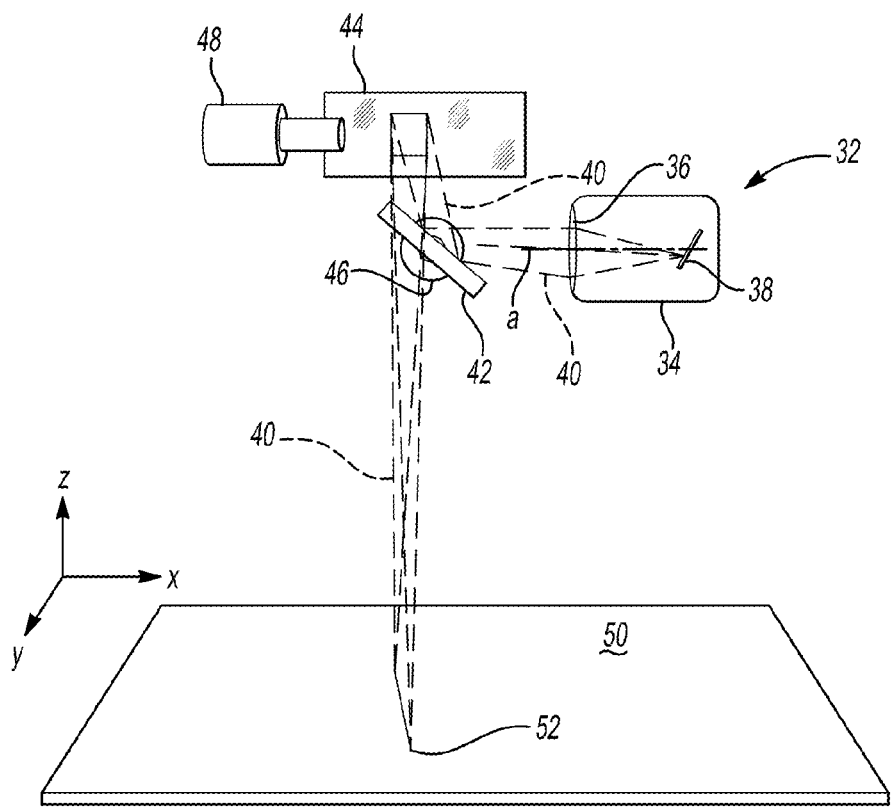
FIG. 3 shows the galvanometer scanned camera assembly of the present invention.

A galvanometer scanned camera of the present invention is generally shown at 32 in FIG. 3. A camera assembly 34 includes an optical lens 36 and a sensor array 38. The sensor array is either a charge coupled device (CCD) or complimentary metal-oxide-semiconductor (CMOS) sensor array, each containing an array of pixels capable of capturing images from reflective light as is known of ordinary skill in the art. The optical lens 36 defines an optical axis a. The sensor array 38 is disposed at an angle offset from the optical axis as will be explained further herein below. The optical lens 36 defines a field of view 40 that is reflected off a first mirror 42 and a second mirror 44. The first mirror 42 is actuated by galvanometer 46 and the second mirror 44 is actuated by a second galvanometer 48 for redirecting the focal point of the camera 34 along an x and y axis of a cartesian coordinate system. Therefore, the field of view 40 of the lens is reflected off the first mirror 42 and subsequently the second mirror 44 and onto a surface of a workpiece 50. It should be understood by those of ordinary skill in the art that a single galvanometer scanning mirror may also be used in some applications.

The anticipated distance from a workpiece 50 is used determine the optimum angle of inclination of the sensor array 38 to the axis a of the optical lens 36. Therefore, the angle of inclination of the sensor array 38 relative to the axis a is correlated to an expected range of the distance of the workpiece from the camera 34. The greater the expected range in distance of the workpiece 50 is from the camera 34, the greater the angle of inclination required to achieve the desired range of focus from the sensor array 38. A larger sensor array would not require the same degree of inclination as does a small sensor because it covers a greater distance range at a lesser degree of inclination.

The camera assembly 34 is also interfaced with CAD data of the workpiece 50 being scanned. Therefore, the camera is even more able to rapidly generate a high resolution image of the area of interest of the workpiece 50. For example, the CAD data detailing a location of an area of interest, such as, for example, a rivet, on an aircraft is signaled to the galvanometers 46, 48 for moving the respective mirrors 42, 44 to a position and orientation that ensures the feature of interest is positioned on sensor array 38 known to provide the most precisely focused, highest resolution image based upon the expected distance to the area of interest.

The inventive arrangement of the galvanometer scanned camera assembly 32 enables an image to be generated along three axis merely by rotating the orientation of the first mirror 42 and the second mirror 44 relative to the optical axis a of the optical lens 36. Cooperatively pivoting the first mirror 42 and a second mirror 44, the focal point 52 is moved in the x and y direction onto a location of interest of the work piece 50. Due to the angular relationship of the sensor array 38 to the optical axis a, the location at which an image is received onto pixels (not shown) of the sensor array 38 now focuses the focal point 52 along z axis enabling the assembly to generate high resolution images of the area of interest of the workpiece in three axis.

Figure 4A:
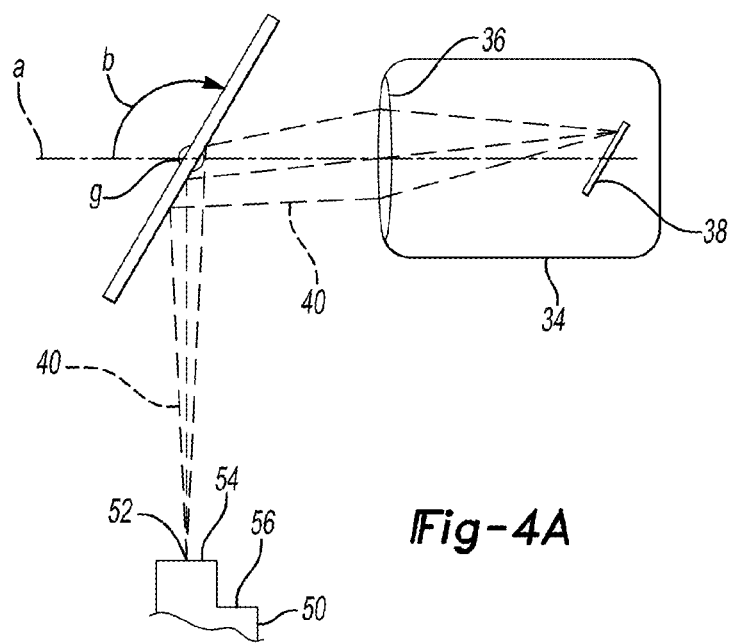
FIGS. 4a and 4b show a schematic of a galvanometer adjustment of the focus of the galvanometer scanned camera of the present invention.
Figure 4B:
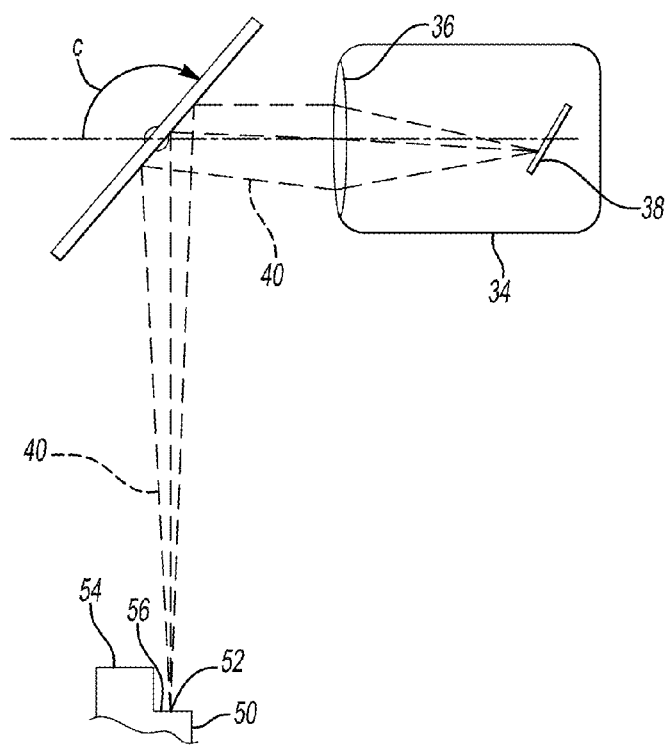

The process of generating a high resolution image upon the sensor array 38 is further understood by reviewing FIGS. 4a and 4b. To generate a high resolution image of a three-dimensional workpiece 50, at least one of the two galvanometer-driven mirrors 42, 44 is pivoted upon galvanometer axis g in a known manner. For ease of understanding, the following is described with a single galvanometer-driven mirror 42. However, it should be understood to those of ordinary skill in the art that a second mirror 42 may also be used for the purpose of moving the focal point 52 of the camera 34. The workpiece 50 represented in FIGS. 4a and 4b includes a first surface 54 and a second surface 56. The second surface 56 is further than the first surface 54 from the camera 34.

Rotating the first mirror 42 around galvanometer axis g to an angle b from the optical axis a projects the focal point of the camera 34 upon first surface 52 of the work piece 50. Based upon the optics of the optical lens 36 and the angular relationship of the sensor array 38 where the most precisely focused, highest resolution image is generated by the pixels disposed on the sensor array 38 most distant from the optical lens 36. An area of interest of the workpiece 50 that is more distant from the camera 34 is represented by second surface 56. In this example, the first mirror 42 is pivoted around galvanometer axis g moving the high resolution projection upon pixels of the sensor array 38 closer to the optical lens 36. In this manner, merely by pivoting the first mirror 42 galvanometer axis g a more distant focal point 52 disposed upon second surface 56 of workpiece 50 is projected on that portion of the sensor array 38 that provides the highest resolution image of the area of interest. Rapidly rotating the first mirror 42 and the second mirror 44 around galvanometer axis g enables the image of camera 34 to be arbitrarily repositioned to a desired area of interest while simultaneously being precisely focused, in an operation requiring only a few hundred microseconds to generate the desired high resolution image.

Figure 5:
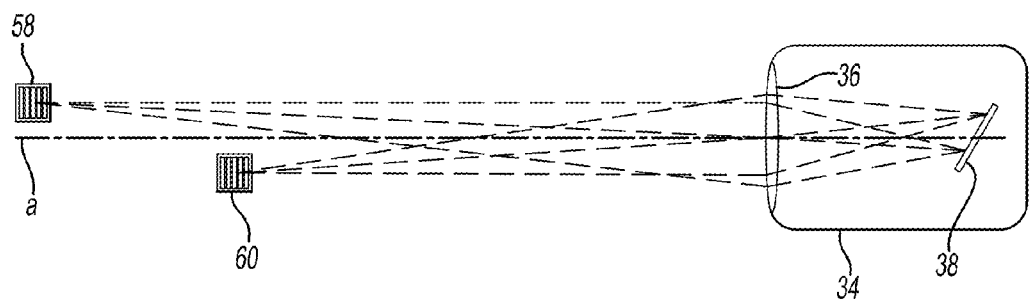
FIG. 5 shows a schematic of an arrangement to demonstrate the effect of the variable focus of the inclined sensor by imaging two optical test targets at varying distance from the camera lens.
Figure 6:
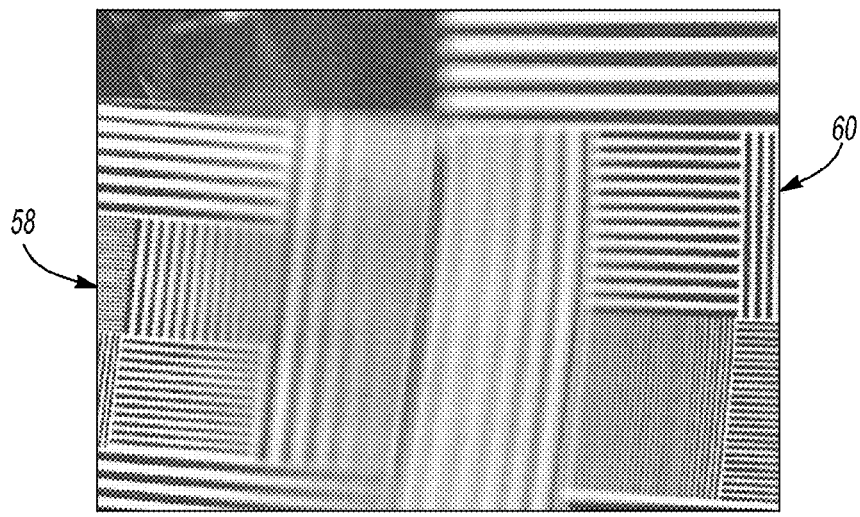
FIG. 6 shows an image generated by a sensor array corresponding to the arrangement of FIG. 5.

It should be understood by those of ordinary skill in the art that a range of focus is continuous across the sensor array. This is best represented in FIG. 5. In this example, the galvanometer-scanned mirrors are removed for simplicity. As explained in detail above, the optical lens 36 defines an optical axis a. The sensor array 38 is offset on an angle from optical axis a so that a variation of pixels disposed in the sensor array 38 have varying distances from the optical lens 36. For clarity, the camera includes a field of view disposed upon two optical resolution test patterns positioned at the limits of the desired inspection distance range, generating the image represented in FIG. 6. First location 58 is more distant than second location 60 while disposed upon the test pattern 62 shown in FIG. 6. When the light reflected from the first and second location 58, 60 passes through optical lens 36, it is projected upon the different locations of the sensor array 38. For example, the pixels disposed upon the sensor array 38 that are near to the optical lens 36 generate the highest resolution image of the more distant, first location 58. Pixels disposed upon the sensor array 38 more distant from the optical lens 36 generate a highest resolution image of the less distant, second location 60. Referring to FIG. 6, the low resolution region disposed between the first and second locations 58, 60 is out-of-focus based upon its disposition relative to the optical lens 36. The out-of-focus area of the image can be cropped as explained below.

Out of focus areas of the image are also of interest. In the example above, an out of focus image is generated of the area of interest of the workpiece 50. The distance of the workpiece 50 from the camera assembly 34 is ascertainable when calculating the corrective measures to bring the area of interest into the desired resolution. In this manner, the galvanometer assembly 32 and the camera assembly 34 is calibrated to the workspace in which they operate.

Figure 7:
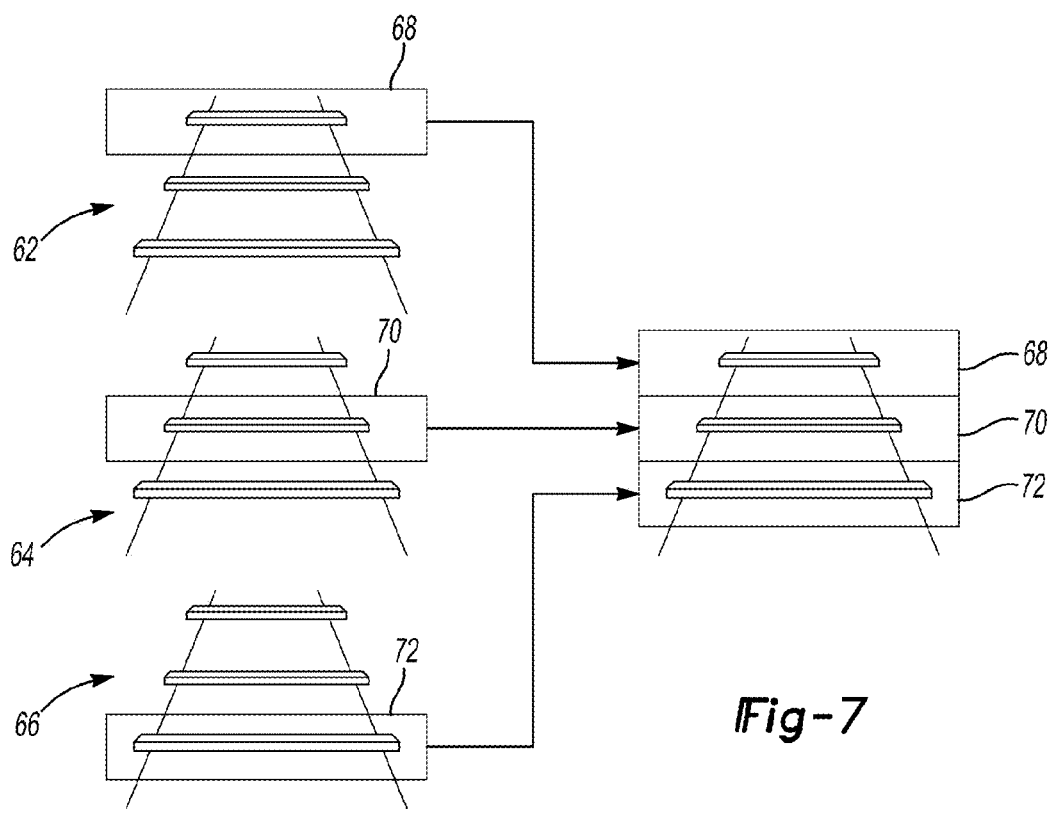
FIG. 7 shows a schematic of a process whereby a plurality of images are combined into a composite image.

It should be understood by those of ordinary skill in the art that the camera assembly 34 rapidly captures multiple images that a have high resolution and, based upon the speed of the galvanometers 46, 48 is capable of rapidly generating multiple images of an area of interest. As such, the assembly is capable of creating a composite image from varying bands capable of simulating an image-capture as specified focus settings. The integration of high-contrast data from all image zones could produce a multi-focal image that provides resolution and detail over a large depth of field not easily obtained using any other optical techniques. As such, a plurality of images is combined to create a focused composite image of high resolution areas of interest. This is best represented in FIG. 7. A first image 62, a second image 63, and a third image 64 are generated by the sensor array 38 of an area of interest in a three-dimensional workpiece. Based upon the angular relationship of the sensor array 38 to the optical axis a, a sufficiently high resolution portion of the image generated by the sensor array 38 is identified in each image element number 68, 70, and 72. These sections 68, 70, and 72 are compiled into a composite image generating a broad range of high resolution image providing an broadened inspection area of the workpiece 50.

Figure 8:
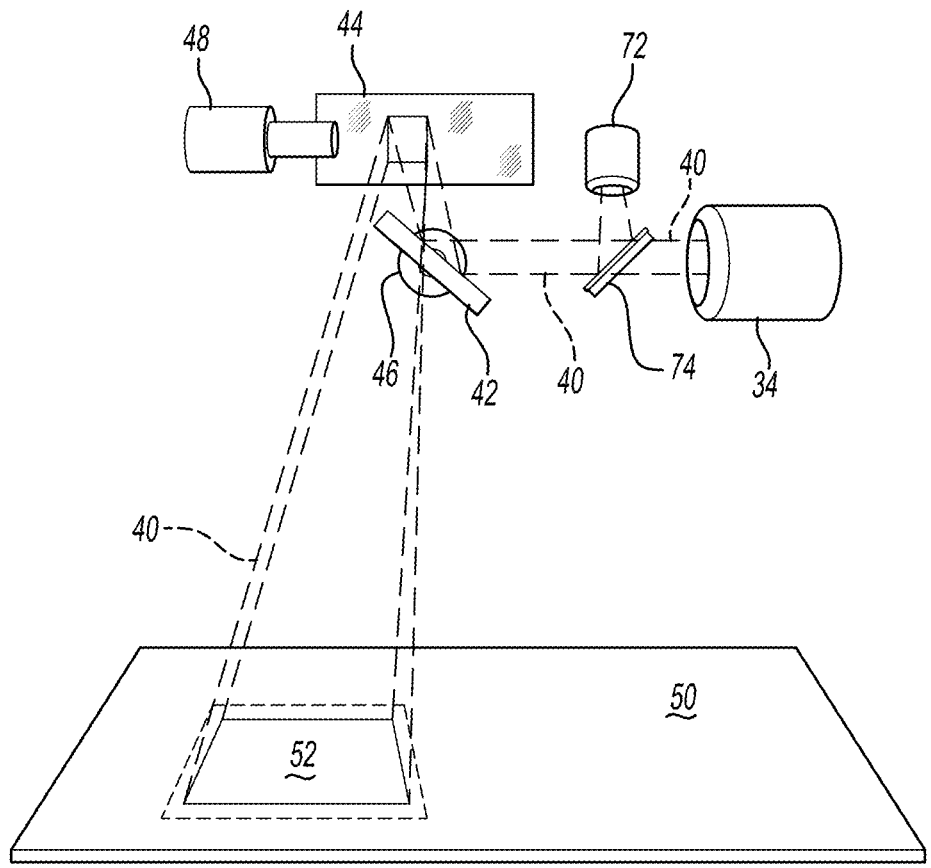
FIG. 8 shows an alternative embodiment of the present invention whereby an illumination source is included with the galvanometer scanned camera of the present invention.

A further embodiment of the present invention is generally shown at 70 of FIG. 8 wherein like element numbers of like elements of the prior embodiments are retained. In some applications, it is desirable to include a lighting source 72. The lighting source is contemplated by the inventor to take the form of a Cree Xlamp XP-E high intensity LED collected by an aspheric condenser lens. However, it should be understood by those of skill in the art that equivalent lighting sources are also considered within the scope of this invention. A beam splitter 74 is positioned within the field of view 40 of the camera assembly 34 at an angle calculated to project light generated by the lighting source 72 coincident to the field of view 40 of the camera assembly 34. Therefore, the lighting source 72 directs light along the field of view 40 of the camera by reflecting light off the first mirror 42 and the second mirror 44 onto the area of interest of the workpiece 50. Therefore, the area of illumination is always appropriate for the camera 34 view. This arrangement provides for highly concentrated illumination allowing for short camera exposure intervals for further improving image resolution exceeding ambient light conditions. In an additional enhancement, the light source 7 can be monochrome. Further, a light filter can be positioned between in the field of view 40 of the camera to filter ambient light, but only allow illumination light having the wavelength of the light source 72 to enter the camera assembly 34.

The camera assembly 32 of the present invention is also combinable with a scanned laser system using galvanometer driven mirrors that are cooperable with the mirrors 42, 44 and galvanometers 46, 48 for rapid refocusing through triangulation. Therefore, range estimation for optimal high resolution focus with the laser scanner is achieved from an out of focus image on the workpiece 50 generated by the laser scanner allowing the computer to calculate the required offset position of the sensor array 38 to bring the area of interest 52 into desired high resolution focus. This configuration provides for continuous and precise focus adjustment without requiring movable parts other than the galvanometers 46, 48.

Obviously, many modifications and variations of the present invention are possible in light of the above teachings. The foregoing invention has been described in accordance with the relevant legal standards; thus, the description is exemplary rather than limiting in nature. Variations and modifications to the disclosed embodiment may become apparent to those skilled in the art and do come within the scope of the invention. Accordingly, the scope of legal protection afforded this invention can only be determined by studying the following claims.

The invention claimed is:

1. A method for inspecting a workpiece by generating a high resolution image, comprising the steps of:
providing a sensor array and an optical lens defining an optical axis for focusing a view of the workpiece onto said sensor array;
providing a mirror assembly having an orientation for redirecting the view of said sensor array;
inclining said sensor array relative to said optical axis of said optical lens;
altering the orientation of said mirror assembly for directing the view of said sensor array to an area of interest on the workpiece and said optical lens directing the view of the area of interest to a portion of said sensor array determined to increase resolution of an image generated of the area interest on the workpiece based upon the angle of incline of said sensor array relative to said optical axis.

2. The method set forth in claim 1, wherein said step of providing a mirror assembly is further defined by providing a galvanometer oriented mirror.

3. The method set forth in claim 1, wherein said step of providing a mirror assembly is further defined by providing a plurality of galvanometer oriented mirrors.

4. The method set forth in claim 1, further including the step of directing light that is coincident with a path of view of said image sensor.

5. The method set forth in claim 4, wherein said step of directing light is further defined by directing light generated by an LED light source concentrated by collecting optics.

6. The method set forth in claim 4, wherein said step of directing light that is coincident with a path of view of said image sensor is further defined by combing a beam of said light and said path of view of said image sensor with a beam splitter.

7. The method set forth in claim 1, wherein said step of focusing a view of the workpiece onto said sensor array is further defined by adjusting said mirror assembly while maintaining said optical lens and said sensor array in a fixed position.

8. The method set forth in claim 1, further including the step of combining multiple images sensed by said sensor array into a composite image for increased field of inspection.

9. The method set forth in claim 1, further including the step of focusing said sensor array on a plurality of locations of the workpiece wherein the plurality of locations of the workpiece have varying distances from said sensor array.

10. The method set forth in claim 1, further including the step of providing an illumination source emitted from a location different from said sensor array and the workpiece for enhancing the resolution of the image generated of the area of interest on the workpiece.

11. The method set forth in claim 1, further including the step of providing CAD data of the workpiece for predetermining the desired field of view of the optical lens and directing the mirror assembly to focus the field of view of the optical lens onto the desired field of view determined to increase resolution of an image generated of the area interest on the workpiece based upon the angle of incline of said sensor array relative to said optical axis as determined by the CAD data.

12. The method set forth in claim 1, further including the step of projecting a laser pattern onto the workpiece having a known offset position from the workpiece for calculating a offset distance to the projected laser pattern, and repositioning the image on the sensor array by adjusting the mirror assembly for providing a correctly focused image of the projected laser pattern.

13. A camera assembly for generating a high resolution image of an area of interest on a workpiece, comprising:
a sensor array for receiving light reflected from a workpiece;
an optical lens for focusing light reflected from the workpiece onto said sensor array for generating an image of an area of interest of the workpiece, said optical lens defining an optical axis;
a mirror assembly oriented for directing a field of view of said optical lens toward the area of interest on the workpiece thereby translating light reflected from the area of interest of the workpiece onto said sensor array; and
said sensor array being disposed in a fixed position relative to said optical lens and being inclined relative to said optical axis thereby providing varying degrees resolution relative to a distance of the area of interest of the workpiece from said camera assembly enabling said camera assembly to generate high resolution images at varying distances from said camera assembly without adjusting said optical lens relative to said sensor array.

14. The assembly set forth in claim 13, wherein said mirror assembly comprises a galvanometer controlled mirror for moving said field of view of said optical lens along a surface of the workpiece.

15. The assembly set forth in claims 13, wherein said mirror assembly comprises cooperable galvanometer controlled mirrors for moving said field of view of said optical lens in two directions along a surface of the workpiece.

16. The assembly set forth in claim 13, wherein said mirror assembly comprises a pair of galvanometer controlled mirrors cooperably moving a focal length of a focal point of said optical lens.

17. The assembly set forth in claim 13, wherein said sensor array includes an angle of inclination being correlated to a distance of the workpiece from said camera assembly.

18. The assembly set forth in claim 13, further including a light source being substantially coincident with said field of view of optical lens.

19. The assembly set forth in claim 18, further including a beam splitter for directing light generated by said light source in a direction coincident to said field of view of said optical lens.

20. The assembly set forth in claim 18, wherein said light source comprises one of a laser or a concentrated, high intensity light emitting diode.

21. The assembly set forth in claim 13, wherein said sensor array generates a plurality of overlapping images for generating a composite having combined regions of optical focus.

22. The assembly set forth in claim 13, wherein said sensor array comprises one of a charge coupled device or complementary metal-oxide semiconductor.

* * * * *